(12) United States Patent
Ogawa et al.

(10) Patent No.: US 10,195,768 B2
(45) Date of Patent: *Feb. 5, 2019

(54) METHOD OF MANUFACTURING MOLD AND METHOD OF MANUFACTURING PATTERN SHEET

(71) Applicant: FUJIFILM Corporation, Tokyo (JP)

(72) Inventors: Shotaro Ogawa, Kanagawa (JP); Aya Mochizuki, Kanagawa (JP); Atsushi Fujita, Kanagawa (JP); Toshihiro Usa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 148 days.

This patent is subject to a terminal disclaimer.

(21) Appl. No.: 15/286,524

(22) Filed: Oct. 5, 2016

(65) Prior Publication Data

US 2017/0095947 A1    Apr. 6, 2017

(30) Foreign Application Priority Data

Oct. 6, 2015   (JP) .................. 2015-198256

(51) Int. Cl.
*B29C 33/38* (2006.01)
*A61M 37/00* (2006.01)
(Continued)

(52) U.S. Cl.
CPC ..... *B29C 33/3857* (2013.01); *A61M 37/0015* (2013.01); *B29C 33/405* (2013.01); *B29C 33/42* (2013.01); *B29C 33/424* (2013.01); *B29C 33/442* (2013.01); *B29C 39/003* (2013.01); *B29C 39/026* (2013.01); *B29C 39/24* (2013.01); *B29C 39/26* (2013.01); *B29C 39/36* (2013.01);
(Continued)

(58) Field of Classification Search
CPC .................................................. B29C 33/3857
See application file for complete search history.

(56) References Cited

U.S. PATENT DOCUMENTS 10,029,081 B2    7/2018   Che et al.
2009/0194908 A1   8/2009   Chen et al.

FOREIGN PATENT DOCUMENTS

EP    2921201    9/2015
EP    2921202    9/2015
(Continued)

OTHER PUBLICATIONS

"Search Report of Europe Counterpart Application", dated Feb. 6, 2017, p. 1-p. 9.
(Continued)

*Primary Examiner* — Timothy Kennedy
(74) *Attorney, Agent, or Firm* — JCIPRNET

(57) ABSTRACT

There is provided a method capable of manufacturing a mold at low cost, and a method of manufacturing a biocompatible pattern sheet by using the mold. The method of manufacturing a mold having a recessed pattern includes the steps of: forming a silicone resin film by applying a silicone resin solution to a surface of a model having a protrusion pattern; defoaming the silicone resin film by reducing the silicone resin film in pressure; forming the mold by heating and curing the silicone resin film while a base plate is in contact with a face of the silicone resin film, the face being opposite to the model; and releasing the mold from the model after releasing the base plate. The method of manufacturing a pattern sheet uses the mold.

8 Claims, 7 Drawing Sheets

(51) Int. Cl.
| | |
|---|---|
| *B29C 33/40* | (2006.01) |
| *B29C 33/42* | (2006.01) |
| *B29C 39/00* | (2006.01) |
| *B29C 39/02* | (2006.01) |
| *B29C 39/24* | (2006.01) |
| *B29C 39/26* | (2006.01) |
| *B29C 39/36* | (2006.01) |
| *B29C 33/44* | (2006.01) |
| *B29K 83/00* | (2006.01) |
| *B29K 105/00* | (2006.01) |
| *B29L 31/00* | (2006.01) |
| *B29C 33/30* | (2006.01) |

(52) U.S. Cl.
CPC .... *A61M 2037/0053* (2013.01); *B29C 33/301* (2013.01); *B29C 2791/006* (2013.01); *B29K 2083/00* (2013.01); *B29K 2105/0035* (2013.01); *B29K 2883/00* (2013.01); *B29K 2883/005* (2013.01); *B29L 2031/756* (2013.01); *B29L 2031/7544* (2013.01)

(56) References Cited

FOREIGN PATENT DOCUMENTS

| | | |
|---|---|---|
| EP | 3006078 | 4/2016 |
| JP | 2009207733 | 9/2009 |
| JP | 2010069252 | 4/2010 |
| JP | 2010247479 | 11/2010 |
| JP | 2011224332 | 11/2011 |
| JP | 2015-100401 | 6/2015 |
| JP | 2015104481 | 6/2015 |
| JP | 2015136528 | 7/2015 |
| WO | 2014077243 | 5/2014 |
| WO | 2014196522 | 12/2014 |

OTHER PUBLICATIONS

Dow Corning, "Product Information Sylgard 184 Silicone Elastomer", Jan. 1, 2007, Available at: http://research.engineering.ucdavis.edu/ncnc/wp-content/uploads/sites/11/2013/05/Sylgard_184_data_sheet.pdf.

"Office Action of U.S. Appl. No. 15/286,515," dated May 11, 2018, p. 1-p. 15.

"Office Action of Japan Counterpart Application," dated Oct. 30, 2018, with English translation thereof, p. 1-6.

METHOD OF MANUFACTURING MOLD AND METHOD OF MANUFACTURING PATTERN SHEET

CROSS-REFERENCE TO RELATED APPLICATIONS

The present application claims priority under 35 U.S.C. § 119 to Japanese Patent Application No. 2015-198256 filed on Oct. 6, 2015. The above application is hereby expressly incorporated by reference, in its entirety, into the present application.

BACKGROUND OF THE INVENTION

Field of the Invention

The present invention relates to a method of manufacturing a mold and a method of manufacturing a pattern sheet, and more particularly to a method of manufacturing a mold and a method of manufacturing a pattern sheet in which a silicone resin is used as a material of the mold.

Description of the Related Art

Conventionally, most of the methods of applying medicine through a surface of a living body, such as skin and mucosa, are methods of adhesion of a liquid substance or a powdery substance. Unfortunately, since an adhesion area of these substances is limited to a surface of skin, an attached medicine and the like may be removed due to sweating or contact with a foreign material, whereby it is difficult to apply a proper amount of medicine. In such a method using permeation caused by diffusion of medicine, it is difficult to reliably control permeation depth to allow medicine to deeply permeate skin, whereby it is difficult to acquire a sufficient medical effect.

For this reason, a transdermal absorption sheet having a needle-like protruding section with a high aspect ratio (also referred to as fine needles or micro needles) containing medicine, is used for a method of injecting the medicine into skin by inserting the fine needles into the skin.

As a method of manufacturing a functional film having this kind of structure with a high aspect ratio, Japanese Patent Application Laid-Open No. 2009-207733 (Patent Literature 1), for example, describes a method of manufacturing a duplicate by transferring a metal mold provided with needle-like objects, and manufacturing needle-like objects having structure with a high aspect ratio by transfer molding using the duplicate.

SUMMARY OF THE INVENTION

However, the method of manufacturing needle-like objects described in Patent Literature 1 is unsuitable for mass production. It is important to mass-produce a pattern sheet with a protrusion pattern, that is, to uniformly manufacture a pattern sheet at low cost with high productivity. Particularly, there is not sufficient examination with regard to (1) a method of rapidly manufacturing a pattern sheet with a large area, (2) a method of manufacturing a pattern sheet without any defects, and (3) a method of manufacturing a biocompatible pattern sheet, and a technique of manufacturing large numbers of molds at low cost has been desired.

The present invention is made in light of the above-mentioned circumstances, and aims to provide a method capable of manufacturing a mold at low cost, and a method of manufacturing a biocompatible pattern sheet by using the mold.

To achieve the object above, the present invention provides a method of manufacturing a mold having a recessed pattern, the method including the steps of: applying a thermosetting resin solution to a surface of a model (male mold) having a protrusion pattern to forming a thermosetting resin film; reducing the thermosetting resin film in pressure to defoam the thermosetting resin film; heating and curing the thermosetting resin film to form the mold (female mold) in a state where a base plate is in contact with a face of the thermosetting resin film, the face being opposite to a face facing the model; and releasing the mold from the model after releasing the base plate from the mold.

According to the present invention, after a thickness of the mold is adjusted by using the base plate, the base plate is released before the mold is released from the model, and then the mold is released. Thus, it is possible to prevent the mold from tearing or being deformed in shape.

In yet another aspect of the present invention, it is preferable that the model having the protrusion pattern is a metal electroformed model formed by electroforming from a first mold having a recessed pattern which has a reversed shape of the protrusion pattern.

According to this aspect, since an electroformed model formed by electroforming from the first mold serves as the model having a protrusion pattern, a plurality of electroformed models can be formed from the first mold. Thus, manufacturing costs of the model having a protrusion pattern can be reduced to enable manufacturing costs to be reduced as a whole.

In another aspect of the present invention, it is preferable that a separation sheet is provided between the base plate and the thermosetting resin film when the base plate is brought into contact with the thermosetting resin film.

According to this aspect, since the separation sheet is provided between the base plate and the thermosetting resin film, the base plate and the thermosetting resin film can be easily released from each other. Thus, it is possible to prevent the mold from tearing or being deformed in shape when the base plate is released from the mold acquired by curing the thermosetting resin film.

In yet another aspect of the present invention, it is preferable that the model having the protrusion pattern includes a plurality of areas each provided with the protrusion pattern, and that the thermosetting resin solution is applied by a slit nozzle in a width of the protrusion pattern.

According to this aspect, since the thermosetting resin is applied by using a slit nozzle in a width of the protrusion pattern, an extra application of the thermosetting resin solution can be prevented.

In yet another aspect of the present invention, it is preferable that a gap adjustment mechanism which adjusts a distance between the model and the base plate is provided around the model having a protrusion pattern, and that the base plate is brought into contact with the gap adjustment mechanism.

According to this aspect, since the gap adjustment mechanism is provided, a thickness of the thermosetting resin film can be adjusted to a height of the gap adjustment mechanism by bringing the base plate into contact with the gap adjustment mechanism. Accordingly, a thickness of the formed mold can be made uniform by using the gap adjustment mechanism.

In yet another aspect of the present invention, it is preferable that a release assisting frame is disposed around an area of the model where the protrusion pattern is provided, and that the thermosetting resin solution is applied so that at least a part of the release assisting frame is covered with the thermosetting resin solution.

According to this aspect, at the time when the mold is released, by performing the release using the release assisting frame, the mold formed of the thermosetting resin can be reliably released.

To achieve the object above, the present invention provides a method of manufacturing a pattern sheet having a protrusion pattern, the method including the steps of: supplying a polymer solution to a recessed pattern of a mold manufactured by the method of manufacturing a mold described above; drying the polymer solution to form a polymer sheet; and releasing the polymer sheet from the mold.

According to the present invention, since a pattern sheet is manufactured by using the mold described above, it is possible to manufacture the pattern sheet that can be used safely to a living body. In addition, since the mold can be reliably manufactured, a shape of the mold can be made uniform as well as manufacturing costs can be reduced.

In yet another aspect of the present invention, it is preferable that the polymer solution is a water-soluble material.

According to this aspect, since the polymer solution forming the pattern sheet is a water-soluble material, medicine can be easily injected when the protrusion pattern formed on the pattern sheet is inserted into a skin.

In yet another aspect of the present invention, it is preferable that a plurality of the molds are joined to form an assembled mold with an increased area of a face in which the recessed pattern is formed, and then the polymer solution is supplied to the assembled mold in the step of supplying a polymer solution.

According to this aspect, since a pattern sheet is formed after a plurality of molds are joined to form an assembled mold with an increased area, a pattern sheet having a plurality of protrusion patterns can be manufactured in one production of a pattern sheet, whereby the productivity can be improved.

According to the method of manufacturing a mold, and the method of manufacturing a pattern sheet, of the present invention, a mold can be manufactured at low cost, and productivity can be improved. Manufacturing a pattern sheet by using the mold enables to manufacture a pattern sheet that is safe to a living body.

DETAILED DESCRIPTION OF THE PREFERRED EMBODIMENTS

Figure 1:
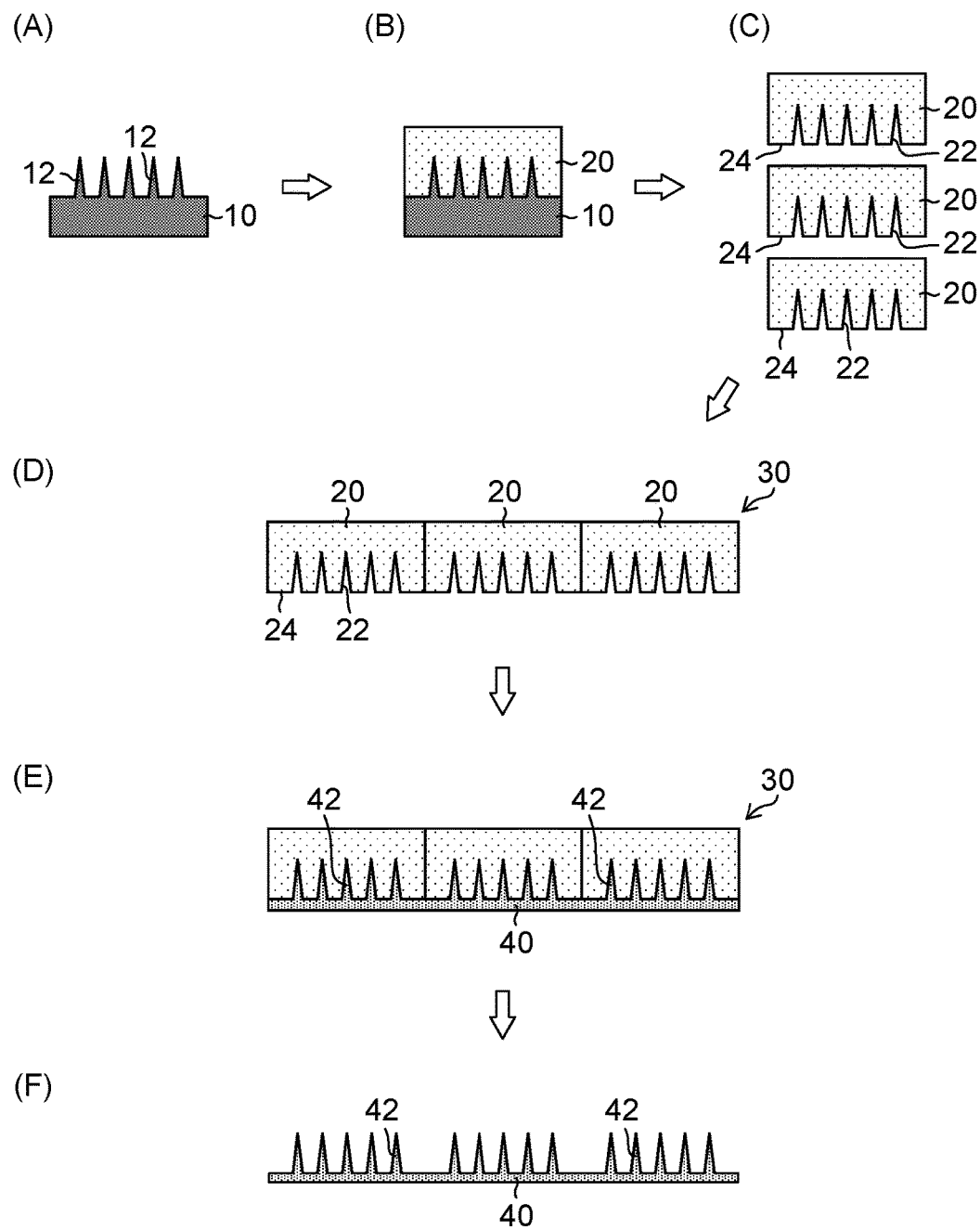
FIG. 1 is a process chart illustrating a procedure of manufacturing a model having a protrusion pattern.

Hereinafter, a method of manufacturing a mold and a method of manufacturing a pattern sheet in accordance with the present invention will be described with reference to accompanying drawings. In the present specification, the term, "to" between numeric values is used so that the numeric values described at the front and back of the term, "to" indicate a lower limit value and an upper limit value, respectively. In addition, an example using silicone resin as an example of thermosetting resin will be described below.

The present invention relates to a technique of manufacturing a mold (female mold) from a model (male mold) provided with a protrusion pattern, the mold having a reversed shape of the protrusion pattern, without a defect, and a technique of manufacturing a pattern sheet being a duplicate of the model provided with the protrusion pattern by using the mold. Specifically, a silicone resin solution for forming a mold is applied on a surface of a model (male mold) 40 having a protrusion pattern 42 to form a silicone resin film 60. Subsequently, the silicone resin film 60 is reduced in pressure to defoam the silicone resin film 60. Then, while a base plate 64 is in contact with a face, which is opposite to the model 40, of the silicone resin film 60, the silicone resin film 60 is heated and cured to form a mold 68. Last, after the base plate 64 is released, the mold (female mold) 68 is released from the model 40 to manufacture the mold 68. In addition, a pattern sheet 76 is manufactured by using the mold 68. As described above, manufacturing the mold 68 by using the silicone resin enables the mold 68 to be manufactured at low cost, as well as the pattern sheet 76 to be manufactured without any defects. In addition, in a case where the pattern sheet is used for micro needles, for example, it is possible to manufacture a pattern sheet that can be used safely to a living body. Each of steps will be described below.

(Method of Manufacturing Mold)

[Step of Manufacturing First Mold]

A first mold 20 includes a recessed pattern 22 having a reversed shape of the model 40 and is used to manufacture the model 40 having the protrusion pattern 42 that has a reversed shape of the mold 68. The first mold 20 is manufactured from a master plate 10 provided with a protrusion pattern 12, by using a resin.

First, as illustrated in Part (A) in FIG. 1, the master plate 10 provided with the protrusion pattern 12 is prepared. A method of manufacturing the master plate 10 provided with the protrusion pattern 12 is not particularly limited, but, for example, the master plate 10 can be manufactured as follows. A plurality of protrusion patterns 12 can be manufactured in a surface of the master plate 10 by cutting a metal base plate, such as Ni, by machine cutting with a cutting tool such as a diamond tool.

In another method, after a photoresist is applied on a Si base plate, the photoresist is exposed and developed. Then, etching such as reactive ion etching (RIE) is applied to a surface of the master plate 10 to form the protrusion pattern 12 in the surface thereof. When etching such as RIE is applied to form the protrusion pattern 12 on the surface of the master plate 10, the protrusion pattern can be formed by applying the etching to the Si base plate in an oblique direction while the Si base plate is rotated.

Next, as illustrated in Part (B) and Part (C) in FIG. 1, a plurality of first molds 20 each having the recessed pattern 22 are manufactured by using the master plate 10. The first mold 20 can be manufactured by the following methods using a resin. In a first method, a silicone resin in which a hardening agent is added into polydimethylsiloxane (PDMS), such as Sylgard 184 of Dow Corning Corp. (Sylgard: registered trademark), is poured to the master plate 10, and is heated at 100° C. and cured, thereby forming the first mold 20 having the recessed pattern 22 from the master plate 10, the first mold 20 having a reversed shape of the protrusion pattern.

In a second method, an ultraviolet light curable resin, which is curable by being irradiated with ultraviolet light, is poured to the master plate 10 and is irradiated with ultraviolet light in a nitrogen atmosphere, and then is the first mold 20 is released from the master plate 10. In a third method, a solution in which a plastic resin, such as polystyrene and polymethyl methacrylate (PMMA), is dissolved in an organic solvent is poured to the master plate 10 being coated with a release agent and is cured by drying so as to volatize the organic solvent, and then the first mold 20 is released from the master plate 10.

It is preferable to use a resin, such as an ultraviolet light curable resin or a thermoplastic resin, as a material forming the first mold 20. Using an ultraviolet light curable resin or a thermoplastic resin enables the first mold 20 to be easily manufactured as well as the protrusion pattern 12 of the master plate 10 to be uniformly formed.

[Step of Manufacturing First Assembled Mold]

Next, as illustrated in Part (D) in FIG. 1, a plurality of first molds 20 manufactured from the master plate 10 are joined to increase an area of a face 24 provided with the recessed pattern 22 of the first mold 20, thereby manufacturing a first assembled mold 30.

The first assembled mold 30 can be manufactured by joining the plurality of first molds 20. The first molds 20 can be joined by using an adhesive, for example. Since the first assembled mold 30 serves as a form of the model 40 having the protrusion pattern 42 to be manufactured in a subsequent step, it is preferable to form the first assembled mold 30 while flatness of the face 24 provided with the recessed pattern 22 is secured. If the flatness of the face 24 provided with the recessed pattern 22 is not secured, a level difference is unfavorably formed in an electroformed model, a mold, and a pattern sheet, which are to be manufactured in subsequent steps.

Although a method of manufacturing the first assembled mold 30 while securing flatness of the recessed pattern 22 is not particularly limited, for example, the flatness of the first assembled mold 30 can be secured by: making the face 24 provided with the recessed pattern 22 of the first mold 20 face down above the base plate, disposing the first mold 20 at a position where the face 24 is brought into contact with the base plate, and adhering the face 24 on the base plate with an adhesive. Since the flatness of the first assembled mold 30 is secured by using the base plate as described above, it is possible to prevent generation of a level difference with an adhesive between the first molds 20 in the first assembled mold 30, a deformation therebetween, and the like, whereby the flatness of the first assembled mold 30 can be secured.

The first assembled mold 30 may be manufactured, but doesn't necessarily have to be manufactured. If the first assembled mold 30 is not manufactured, a model having a protrusion pattern is manufactured from the first mold 20. However, manufacturing the first assembled mold 30 is preferable because a model with a large area can be manufactured by one electroforming. Manufacturing the first assembled mold 30 is also preferable in subsequent steps because a mold can be manufactured by using the model with a large area, and a pattern sheet can be manufactured from the mold to enable productivity of the pattern sheet to be improved.

[Step of Manufacturing Model having Protrusion Pattern]

Part (E) in FIG. 1 illustrates a step of manufacturing the model 40 having the protrusion pattern 42 by using the first assembled mold 30. Hereinafter, a method of manufacturing a model having a protrusion pattern by electroforming will be described, for example.

In the electroforming, first, a conductive treatment is applied to the first assembled mold 30. Metal (e.g. nickel) is spattered on the first molds 20 of the first assembled mold 30, and attached to a surface of each of the first molds 20 of the first assembled mold 30 and the recessed pattern 22.

Next, the first assembled mold having been subjected to the conductive treatment is held at a negative pole. A metal pellet is held in a metal case to serve as a positive pole. The negative pole holding the first assembled mold 30 and the positive pole holding the metal pellet are immersed in electroforming liquid and are energized to embed metal in recessed pattern 22 of the first assembled mold 30 to form the model 40. Then, the model 40 having the protrusion pattern 42 (hereinafter also referred to as an "electroformed model 40") is manufactured by releasing it from the first assembled mold (refer to Part (F) in FIG. 1).

The model 40 having the protrusion pattern 42 is not limited to a model manufactured by the method illustrated in Part (A) to Part (F) in FIG. 1, and a model manufactured by the method of manufacturing the master plate 10 also can be used as the model 40. However, since a finer and more complex pattern shape increases manufacturing cost of the master plate 10, manufacturing a plurality of master plates is costly. In addition, each of the master plates may have a protrusion pattern different in a shape. Thus, as illustrated in Part (A) to Part (F) in FIG. 1, manufacturing the model 40 by manufacturing a plurality of first molds 20 from the master plate 10 enables the model 40 to be manufactured at low cost.

[Step of Forming Silicone Resin Film]

Subsequently, a method of manufacturing a mold by using the electroformed model 40 manufactured as described above will be described. FIGS. 2A to 2D illustrate steps of forming a silicone resin film, and FIGS. 3A to 3E illustrate steps of molding a mold and releasing the mold from the electroformed model. In addition, FIG. 4 is a plan view after a release assisting frame is disposed, and FIG. 5 is a plan view after a silicone resin solution is applied.

Figure 2A:
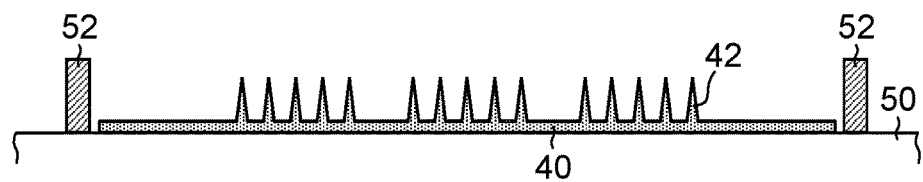
FIGS. 2A to 2D are diagrams illustrating processes in a procedure of forming a silicone resin film.

First, as illustrated in FIG. 2A, the electroformed model 40 is disposed on a base 50. In addition, spacers 52 are disposed outside the electroformed model 40 on the base 50, as gap adjustment mechanisms. The spacers 52 adjust a distance between the electroformed model 40 and the base plate 64 to adjust a thickness of the mold 68 to be manufactured. The spacers 52 are disposed on the base 50. After the silicone resin film is formed, the base plate 64 is brought into contact with the spacers 52 in order to adjust the thickness of the silicone resin film, whereby adjusting the thickness of the mold 68 to be manufactured. While the spacer 52, as illustrated in FIG. 4, is provided outside a central portion of each side of the electroformed model 40 having a quadrangular shape, a portion of each of the spacers 52 is not limited to the above as long as the thickness of the mold can be made uniform when the base plate 64 is brought into contact with the spacers 52. The spacers 52 may be provided all around the electroformed model 40, or may be provided outside respective corners of the electroformed model 40.

The spacer 52 can be made of metal, such as stainless used steel (SUS) and aluminum, and glass. The spacer 52 is preferably made of a material with high rigidity because bringing the base plate 64 into contact with spacer 52 enables thickness of the silicone resin film 60 to be adjusted to a height of the spacer 52.

Figure 2B:
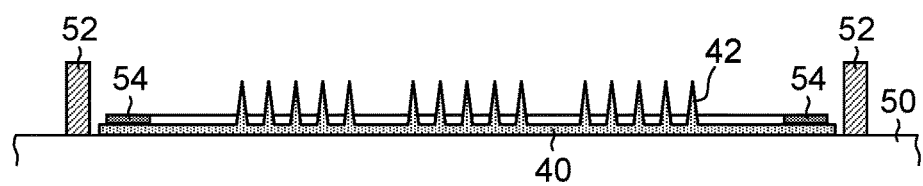
Figure 4:
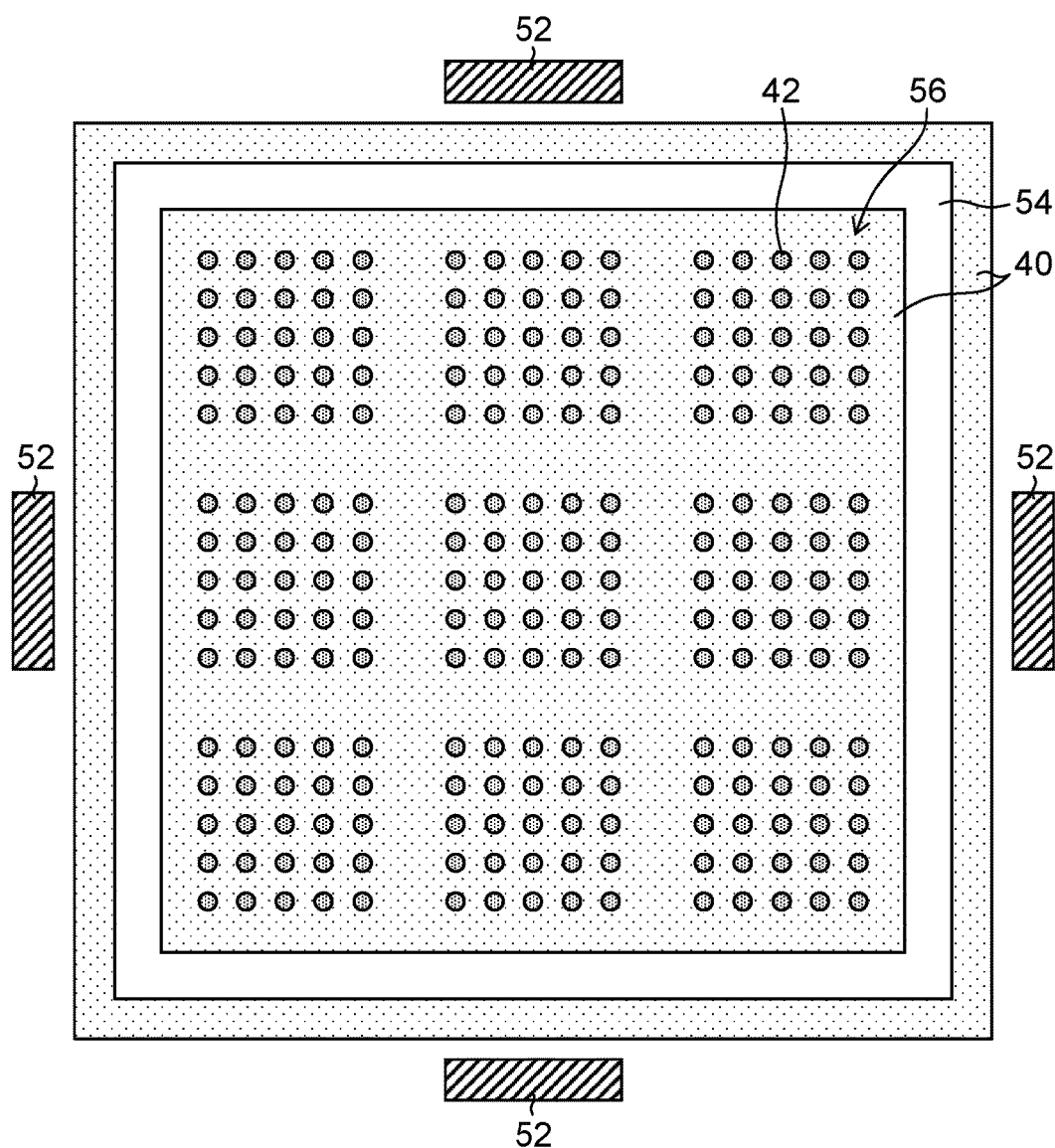
FIG. 4 is a plan view after a release assisting frame is disposed.
Figure 5:
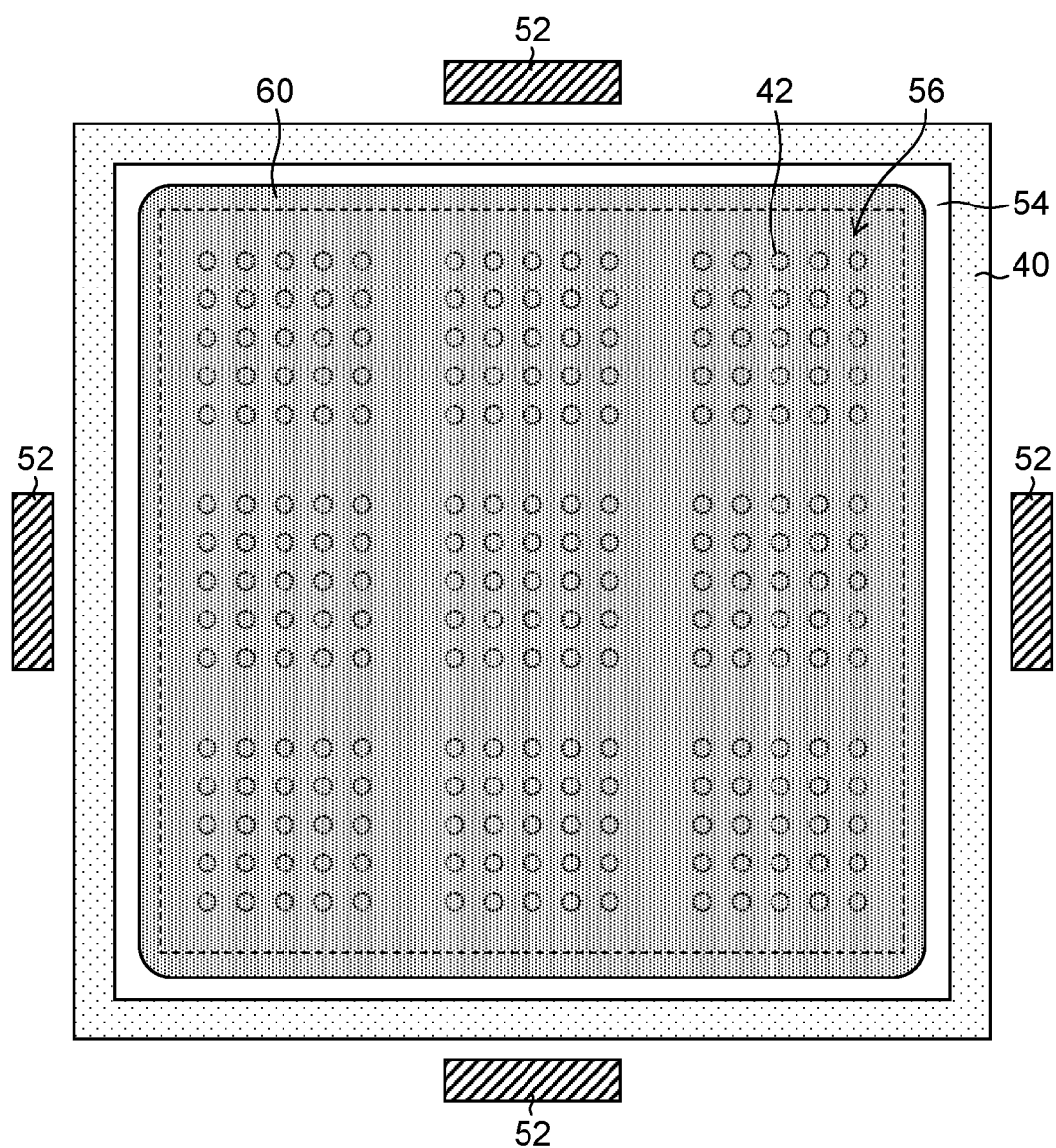
FIG. 5 is a plan view after a silicone resin solution is applied.

As illustrated in FIGS. 2B and 4, a release assisting frame 54 having an opening 56 is provided on the electroformed model 40. The electroformed model 40 is exposed in an area of the opening 56 of release assisting frame 54, and the protrusion pattern 42 of the electroformed model 40 is also disposed in the area of the opening 56 of the release assisting frame 54, that is, inside the release assisting frame 54. The release assisting frame 54 is provided to prevent the mold 68 from tearing when the mold 68 is released from the electroformed model 40. While a position at which the release assisting frame 54 is disposed is not particularly limited, it is preferable that the release assisting frame 54 is provided all around the electroformed model 40, as illustrated in FIG. 4. The mold 68 formed of a silicone resin tends to easily tear due to its low rigidity. Disposing the release assisting frame 54 around the mold 68 enables the mold 68 to be prevented from tearing.

It is preferable to form the release assisting frame 54 in a sheet-like shape, and the release assisting frame 54 can be made of resin such as polyethylene terephthalate (PET), or metal such as SUS and aluminum.

Figure 2C:
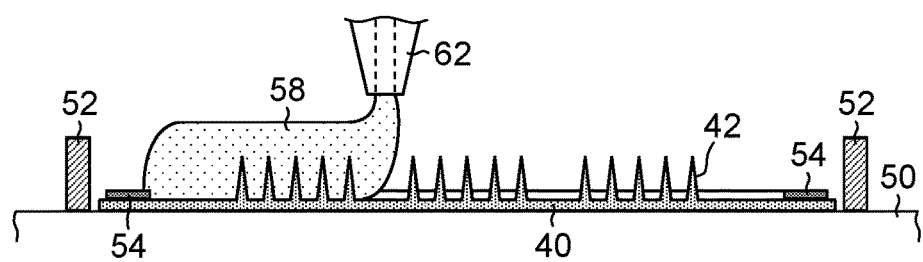
Figure 2D:
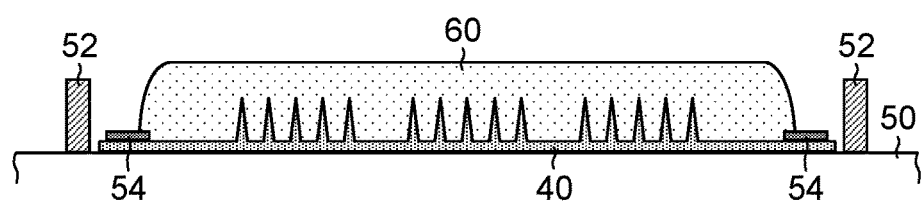

Next, as illustrated in FIGS. 2C and 2D, a silicone resin solution 58 is applied on the electroformed model 40 to form the silicone resin film 60. FIG. 5 is a plan view after the silicone resin film 60 is formed by applying the silicone resin solution 58.

It is preferable that the silicone resin solution 58 is applied to the opening 56 of the release assisting frame 54 so that a part of the release assisting frame 54 is covered with the silicone resin solution 58, as illustrated in FIG. 5. Covering a part of the release assisting frame 54, that is, exposing a part of the release assisting frame 54 enables the mold 68 to be easily released by using the exposed release assisting frame 54.

A method of applying the silicone resin solution 58 is not particularly limited, and an application using a spin coater is available. If there are a plurality of areas in each of which the protrusion pattern 42 is formed, the silicone resin solution 58 can be applied for each area having the protrusion pattern 42 by a slit nozzle 62 in a width of the protrusion pattern 42. Applying the silicone resin solution 58 for each area having the protrusion pattern 42 enables the silicone resin solution 58 to be applied to only a position where a mold is manufactured, whereby an unnecessary application of the silicone resin solution can be prevented.

[Step of Defoaming Silicone Resin Film]

Subsequently, the silicone resin film 60 formed on the electroformed model 40 is reduced in pressure to defoam the silicone resin film 60. Defoaming of the silicone resin film 60 is performed by placing the silicone resin film 60 in a pressure reduction device (not illustrated) together with the base 50, the electroformed model 40, the spacers 52, and the like, and reducing a pressure in the pressure reduction device.

Defoaming of the silicone resin film 60 is checked visually or by image recognition with a charge-coupled device (CCD) camera. Defoaming the silicone resin film 60 enables a shape of the silicone resin film 60 to be uniform at the time of curing the silicone resin.

[Step of Forming Mold]

Figure 3A:
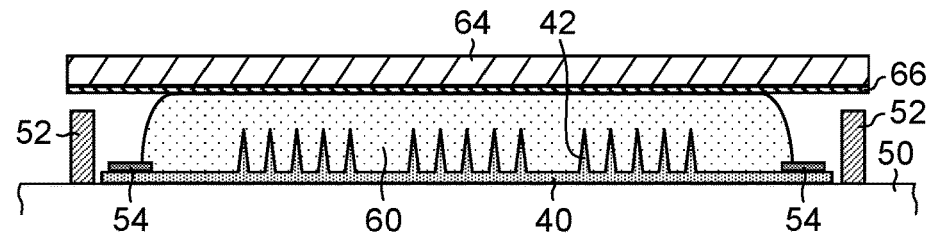
FIGS. 3A to 3E are diagrams illustrating processes in a procedure of manufacturing a mold.
Figure 3B:
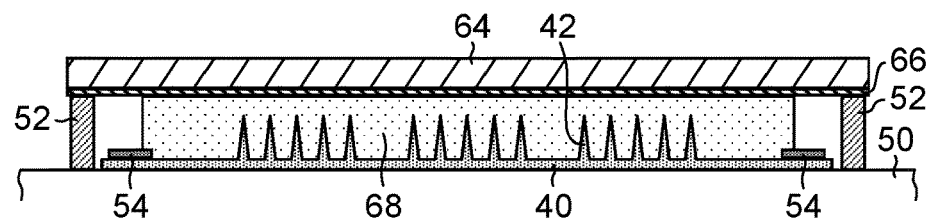

Subsequently, as illustrated in FIG. 3A, the separation sheet 66 disposed on the base plate 64 is brought into contact with a face of the silicone resin film 60, the face being opposite to a face where the silicone resin film 60 is in contact with the electroformed model 40. Then, the base plate 64 is pressed on the spacers 52, as illustrated in FIG. 3B, thereby adjusting the thickness of the silicone resin film 60, that is, the thickness of the mold to be formed.

In addition, it is preferable to provide a separation sheet 66 between the base plate 64 and the silicone resin film 60.

The base plate 64 can be made of metal, such as SUS and aluminum, and glass. When these materials is used for the base plate 64, the mold 68 to be formed can have a uniform height.

In addition, providing the separation sheet 66 between the base plate 64 and the silicone resin film 60 enables the base plate 64 and the silicone resin film 60 to be easily released from each other. Since the base plate 64 is made of the material described above, the base plate 64 is inflexible, and thus it is difficult to release the mold 68 from the electroformed model 40 while the base plate 64 is disposed. Providing the separation sheet 66 enables the mold 68 and the base plate 64 to be easily released from each other, and thus the mold 68 can be released from the electroformed model 40 after the base plate 64 is released. As a result, the mold 68 can be manufactured without a defect and with a uniform shape.

The separation sheet 66 can be made from a fluorocarbon rubber sheet, a Teflon (registered trademark) sheet, a sheet formed by applying a releasing treatment to a silicone resin, or the like.

Then, in a state where the separation sheet 66 disposed on the base plate 64 is in contact with the silicone resin film 60 and the spacers 52, the silicone resin film 60 is heated and cured to form the mold 68. The silicone resin film 60 can be heated with an aluminum heater, an infrared ray heater, a ceramic heater, an induction heating (IH) heater, or the like.

[Step of Releasing Mold]

Figure 3C:
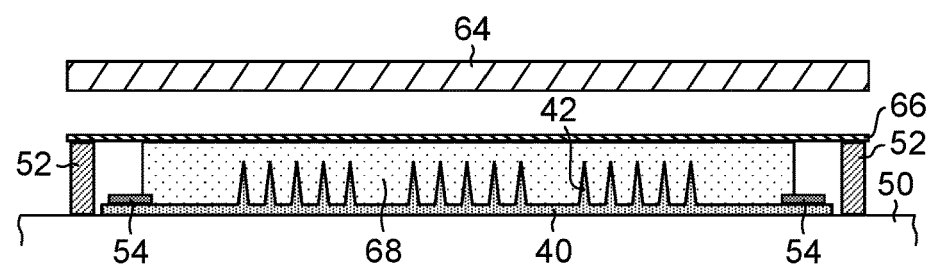
Figure 3D:
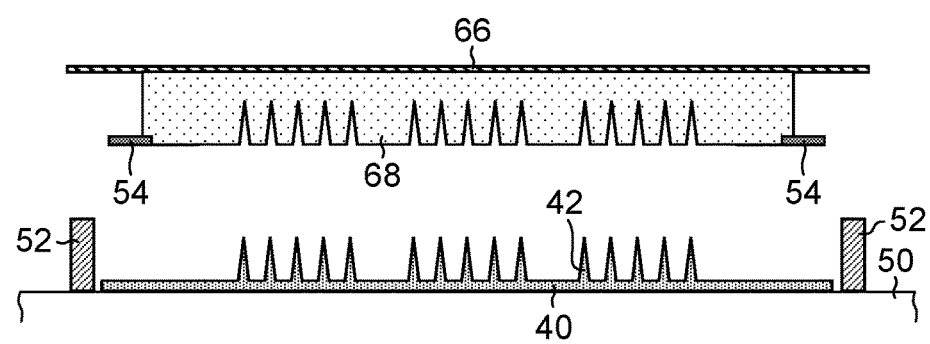
Figure 3E:
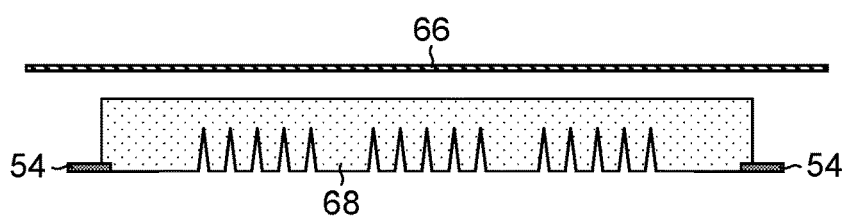

Next, as illustrated in FIGS. 3C and 3D, after the base plate 64 is released, the mold 68 provided with the separation sheet 66 is released from the electroformed model 40. Since the base plate 64 is released firstly, the release assisting frame 54 is disposed and the mold 68 can be released by using the release assisting frame 54, the mold 68 can be released while the mold 68 is prevented from tearing and has a uniform shape. Last, as illustrated in FIG. 3E, the mold 68 having a recessed pattern 70 which has a reversed shape of the protrusion pattern 42 of the electroformed model 40 can be manufactured by releasing the separation sheet 66.

Here, although the release assisting frame 54 is still provided in the mold 68, the manufacturing of pattern sheet, which is explained next, may be performed after cutting off a portion where the release assisting frame 54 is provided from the mold 68, or may be performed in a state where the release assisting frame 54 is provided.

(Method of Manufacturing Pattern Sheet)

Subsequently, a method of manufacturing a pattern sheet by using the mold 68 manufactured by the method of manufacturing described above will be described. FIGS. 6A to 6F are a process chart of manufacturing the pattern sheet 76.

[Step of Supplying Polymer Solution]

Figure 6A:
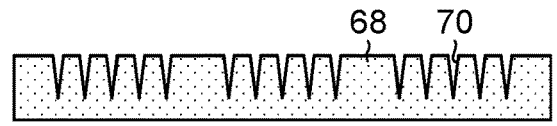
FIGS. 6A to 6F are diagrams illustrating processes in a procedure of manufacturing a pattern sheet.

FIG. 6A illustrates a state where the mold 68 is prepared. The mold 68 is manufactured by the method of manufacturing a mold, described above.

Figure 6B:
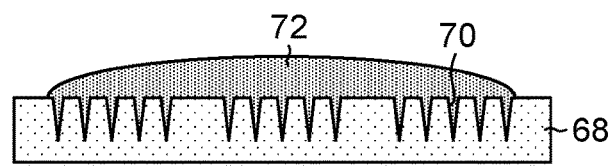

FIG. 6B illustrates a step of supplying a polymer solution 72 to the recessed pattern 70 of the mold 68.

It is preferable to use a water-soluble material as a material forming the pattern sheet 76. In addition, it is preferable to use a biocompatible resin as a resin polymer of the polymer solution to be used for manufacturing of a pattern sheet. As this kind of resin, it is preferable to use a saccharide, such as glucose, maltose, pullulan, sodium chondroitin sulfate, hyaluronate sodium, and hydroxyethyl starch, a protein such as gelatin, or a biodegradable polymer, such as polylactide, and lactic acid-glycolic acid copolymer. Among them, a gelatin-based material can be suitably used because it has adhesion to many base materials, and robust gel strength as a gelling material, so that it can be brought into close contact with a base material, and the pattern sheet 76 can be released by using the base material (not illustrated) when the pattern sheet 76 is released from the mold 68. While concentration of the resin polymer is different depending on material, it is preferable that a concentration of a resin polymer contained in a polymer solution without a medicine is 10 to 50 mass %. In addition, a solvent used for dissolution is not necessarily warm water as long as the solvent has volatility, and thus methyl ethyl ketone (MEK), alcohol, or the like can be used. In a solution of a polymer resin, a medicine to be supplied into the body can be dissolved together in accordance with usage. It is preferable that polymer concentration (concentration of a polymer except a medicine if a medicine itself is a polymer) of the polymer solution containing a medicine is 0 to 30 mass %.

In a case of using a water-soluble high molecule (e.g. gelatin), a method of preparing a polymer solution may include the following: dissolving water-soluble powder in water and then adding a medicine into the solution; and pouring water-soluble high-molecular powder into a liquid in which a medicine is dissolved. If the water-soluble high molecule is difficult to be dissolved in water, it may be dissolved while being heated. It is preferable to heat the water at a temperature of about less than 60° C. while the temperature can be appropriately determined depending on a kind of the high molecular material. A viscosity of the polymer resin solution containing a medicine is preferably 100 Pa·s or less, and more preferably is 10 Pa·s or less. A viscosity of the solution without a medicine is preferably 2000 Pa·s or less, and more preferably is 1000 Pa·s or less. The appropriate adjustment of the viscosity of the polymer resin solution allows the solution to be easily injected into needle-like recessed portions of a mold. For example, the viscosity of the polymer resin solution can be measured with a tube type viscometer, a falling ball viscometer, a rotational viscometer, or a vibration type viscometer.

A medicine to be contained in a polymer solution is not limited if it has a function of a medicine. It is preferable that the medicine is particularly selected from peptide, protein, nucleic acid, polysaccharide, vaccine, a medicinal compound belonging to a water-soluble low-molecular compound, or a cosmetic ingredient.

A method of injecting this kind of resin polymer solution into the mold 68 includes an application using a spin coater, for example.

[Step of Drying]

Figure 6C:
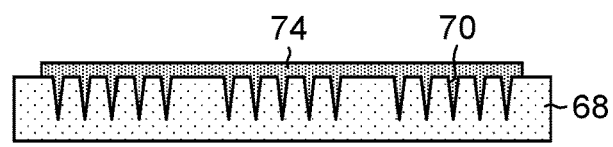

FIG. 6C illustrates a step of drying the polymer solution 72 to form a polymer sheet 74. For example, the polymer solution 72 can be dried by blowing air to the polymer solution 72 supplied to the mold 68. The polymer sheet 74 means the polymer solution 72 in a state after a desired drying process has been applied thereto. The amount of moisture of the polymer sheet 74 and the like are appropriately set. If the amount of moisture of the polymer decreases too much by drying, the polymer sheet 74 tends to be difficult to be released, thus it is preferable to keep the amount of moisture at which an elasticity is maintained.

[Step of Releasing Polymer Sheet]

Figure 6D:
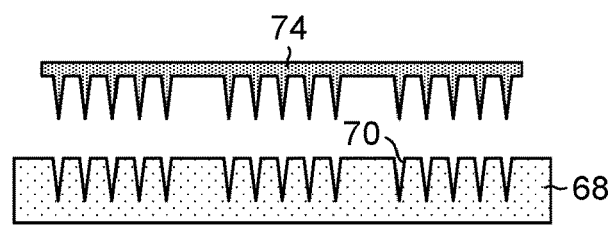
Figure 6E:
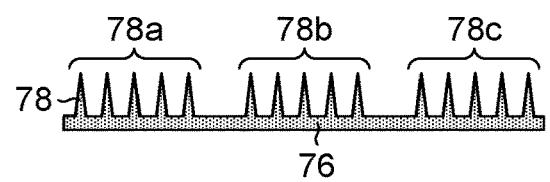
Figure 6F:
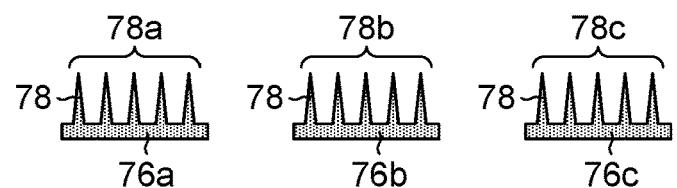

FIGS. 6D and 6E illustrate a state where the polymer sheet 74 is released from the mold 68 to form the pattern sheet 76, and FIG. 6F illustrates a step of cutting the pattern sheet 76 to form individual pattern sheets 76a, 76b, and 76c.

The pattern sheet 76 released from the mold 68 is set in a cutting device (not illustrated), and cutting positions of the pattern sheet 76 are determined. The cutting positions are basically determined so that areas 78a, 78b, and 78c, each having the protrusion pattern 78, are acquired. As illustrated in FIG. 6F, the plurality of individual pattern sheets 76a, 76b, and 76c are formed by cutting the pattern sheet 76.

Figure 7:
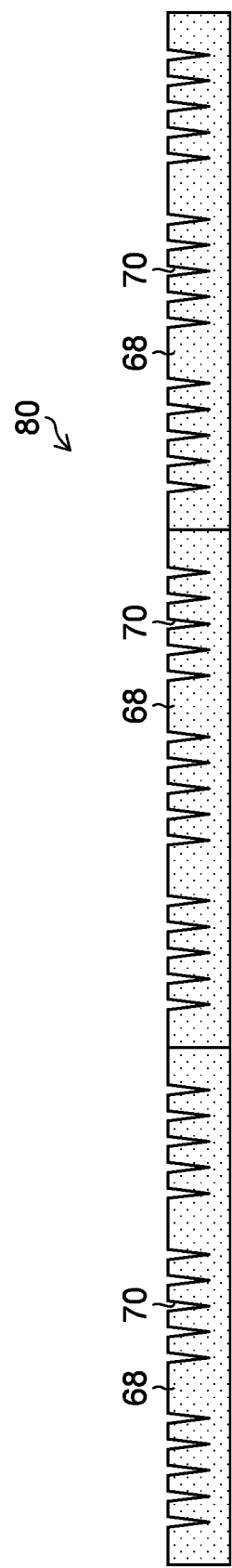
FIG. 7 is a schematic side view of an assembled mold.

While the method of manufacturing the pattern sheet 76 by using the mold 68 is illustrated in FIGS. 6A to 6F, as shown in FIG. 7, the pattern sheet also can be manufactured by manufacturing the assembled mold 80 in which the plurality of molds 68 are joined to have a face with an increased area in which the recessed pattern 70 is formed. The assembled mold 80 can be manufactured by a method similar to the method of manufacturing the first assembled mold, described above.

Manufacturing the pattern sheet by using the assembled mold 80 enables a pattern sheet with a large area to be manufactured by one manufacturing, and thus the productivity can be improved.

In the present embodiment, there is described a case where the polymer sheet 74 is formed by filling the polymer solution 72 into the recessed pattern 70 of the mold 68 and drying the filled polymer solution 72, however, the present invention is not limited to the case.

For example, the recessed pattern 70 of the mold 68 is filled with a polymer solution containing a medicine and the polymer solution is dried, and then the recessed pattern 70 of the mold 68 is filled with a polymer solution containing no medicine and the polymer solution is dried to enable the polymer sheet 74 to be formed.

The mold 68 is sometimes preferable to be used only once and then disposed. In a case where the pattern sheet 76 is used for medical supplies, it is preferable that the pattern sheet is disposable in consideration of safety of the manufactured pattern sheet 76, with respect to a living body. By allowing the mold 68 to be disposable, there is no longer need for cleaning of the mold 68, and thus costs caused by cleaning can be reduced. Particularly, in a case the pattern sheet 76 is used for medical supplies, high detergency is required, which increases cleaning costs.

A shape of a protrusion of the manufactured pattern sheet 76 is not particularly limited as long as a tip tapers. For example, the shape can be a conic shape, or a pyramid shape such as a triangular pyramid and a quadrangular pyramid. In addition, the shape can be formed by a needle section with a tapered shape and a frustum section connected to the needle section.

A height of the protrusion of the protrusion pattern is within a range of not less than 100 μm and not more than 2000 μm, and is preferably within a range of not less than 200 μm and not more than 1500 μm.

Since the manufactured pattern sheet 76 having the protrusion pattern 78 is a duplicate of the model 40 having the protrusion pattern 42, forming a shape of the protrusion pattern 42 of the model 40, or a shape of the protrusion pattern 12 of the master plate 10 in a desired shape enables the manufactured protrusion pattern 78 of the pattern sheet 76 to be formed in the desired shape.

What is claimed is:

1. A method of manufacturing a mold having a recessed pattern, the method comprising:

disposing a release assisting frame around an area of a model where a protrusion pattern is provided;

applying a thermosetting resin solution to a surface of the model having the protrusion pattern so that at least a part of the release assisting frame is covered with the thermosetting resin solution, so as to form a thermosetting resin film;

reducing the thermosetting resin film in pressure to defoam the thermosetting resin film;

heating and curing the thermosetting resin film to form a mold in a state where a base plate is in contact with a face of the thermosetting resin film, the face being opposite to a face facing the model; and releasing the mold from the model with the release assisting frame after releasing the base plate from the mold.

2. The method of manufacturing a mold according to claim 1, wherein the model having the protrusion pattern is a metal electroformed model manufactured by electroforming from a first mold having a recessed pattern which has a reversed shape of the protrusion pattern.

3. The method of manufacturing a mold according to claim 1, further comprising providing a separation sheet between the base plate and the thermosetting resin film when the base plate is moved toward the thermosetting resin film.

4. The method of manufacturing a mold according to claim 1, wherein the model having the protrusion pattern includes a plurality of areas each provided with the protrusion pattern, and the thermosetting resin solution is applied by a slit nozzle in a width of the protrusion pattern.

5. The method of manufacturing a mold according to claim 1, further comprising:

providing a gap adjustment mechanism which adjusts a distance between the model and the base plate around the model having the protrusion pattern; and bringing the base plate into contact with the gap adjustment mechanism.

6. A method of manufacturing a pattern sheet having a protrusion pattern, the method comprising:

supplying a polymer solution to a recessed pattern of a mold manufactured by the method of manufacturing a mold according to claim 1;

drying the polymer solution to form a polymer sheet; and releasing the polymer sheet from the mold.

7. The method of manufacturing a pattern sheet according to claim 6, wherein the polymer solution is a water-soluble material.

8. The method of manufacturing a pattern sheet according to claim 6, wherein in supplying the polymer solution, a plurality of the molds are joined to form an assembled mold with an increased area of a face in which the recessed pattern is formed, and then the polymer solution is supplied to the assembled mold.

* * * * *